(12) United States Patent
Dechev

(10) Patent No.: US 6,961,609 B1  
(45) Date of Patent: Nov. 1, 2005

(54) QUANTITATIVE TITRATION OF THE AUTONOMIC NERVOUS SYSTEM

(76) Inventor: George Dechev, 930 S. Los Robles Ave., Pasadena, CA (US) 91106-3719

( * ) Notice: Subject to any disclaimer, the term of this patent is extended or adjusted under 35 U.S.C. 154(b) by 456 days.

(21) Appl. No.: 10/291,101

(22) Filed: Nov. 7, 2002

(51) Int. Cl.[7] .............................................. A61N 1/30
(52) U.S. Cl. ....................... 604/20; 604/500; 600/309
(58) Field of Search ..................... 604/20, 48, 49, 604/500, 501; 600/309, 310, 312, 348, 362, 600/372, 382, 384, 393, 398

(56) References Cited

U.S. PATENT DOCUMENTS

| | | | |
|---|---|---|---|
| 4,809,707 A * | 3/1989 | Kraft et al. ................. | 600/549 |
| 4,821,733 A * | 4/1989 | Peck ........................... | 600/361 |
| 5,793,292 A * | 8/1998 | Ivey, Jr. ...................... | 340/576 |
| 5,817,012 A * | 10/1998 | Schoendorfer .............. | 600/362 |
| 5,885,211 A * | 3/1999 | Eppstein et al. ............ | 600/309 |
| 6,042,543 A * | 3/2000 | Warwick et al. ............ | 600/362 |
| 6,129,696 A * | 10/2000 | Sibalis ........................ | 604/20 |
| 2004/0236268 A1 * | 11/2004 | Mitragotri et al. ........... | 604/20 |

* cited by examiner

*Primary Examiner*—Sharon Kennedy

(57) ABSTRACT

A non-invasive method for the objective measurement of the functional state of the autonomic nervous system, including the balance between its two divisions, sympathetic and parasympathetic. The method is based on the iontophoretic application of different concentrations of the natural mediators noradrenaline and acetylcholine, and on the visual or instrumental assessment, based on color or conductivity measurement, of the concentrations causing vasoconstriction, and respectively, vasodilatation of the cutaneous vessels.

6 Claims, 1 Drawing Sheet

QUANTITATIVE TITRATION OF THE AUTONOMIC NERVOUS SYSTEM

BACKGROUND

1. Field of Invention

Figure 1:
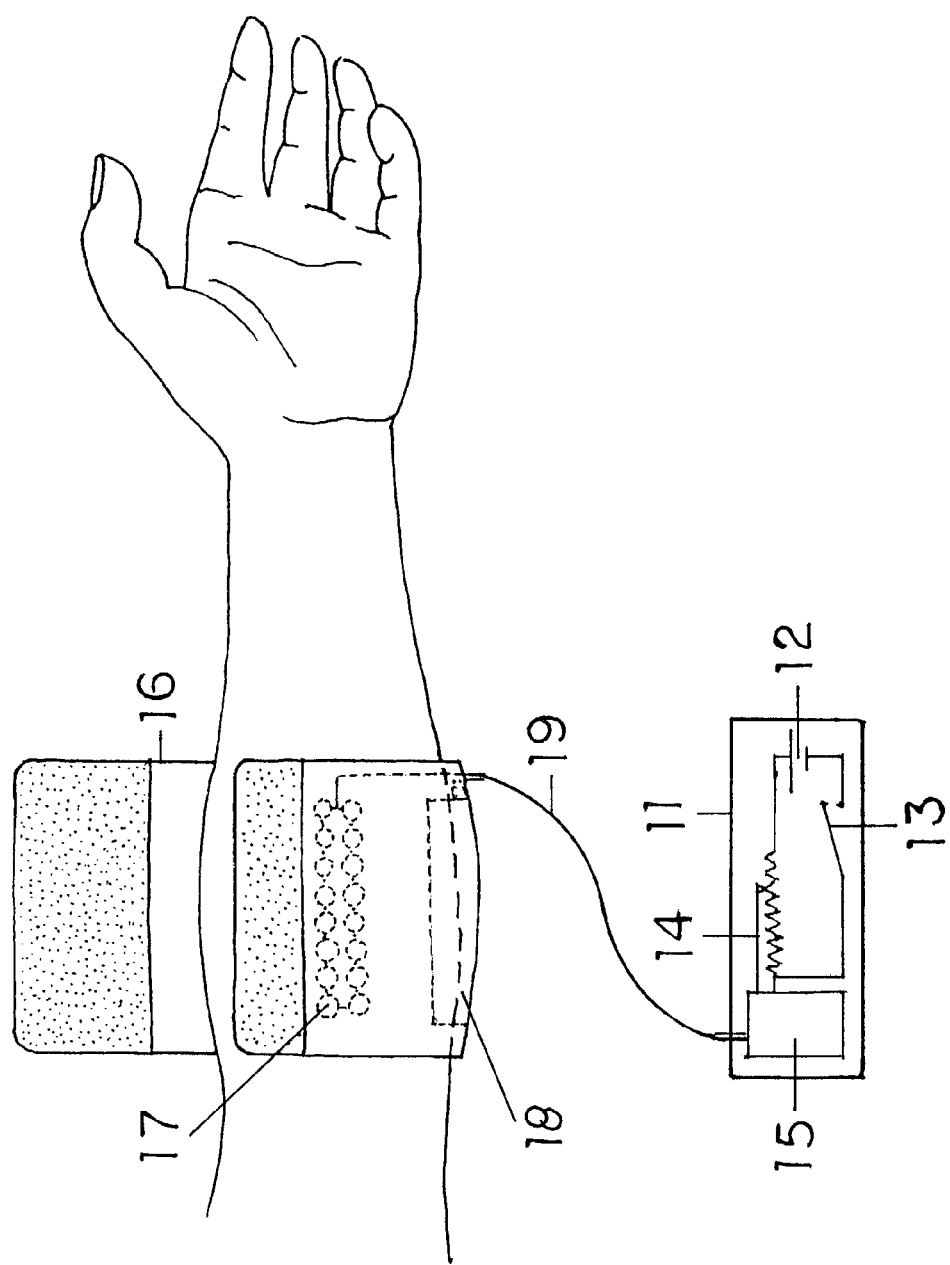

This invention relates to diagnostic biomedical methods.

BACKGROUND

2. Description of Prior Art

Regulating the milieu interne, the autonomic nervous system plays an important role in human health and general condition. Routed in the hypothalamic portion of the diencephalon, peripherally it is distinct in its two divisions: sympathetic and parasympathetic. Most visceral structures receive both sympathetic and parasympathetic innervation. The two divisions of the autonomic nervous system principally act antagonistically; the delicate balance between them regulates many visceral functions.

Dysfunction of the autonomic nervous system is related to many clinical disorders. Angina pectoris which ranks among the most frequent causes of death in the United States, appears to be intimately related to excessive vasoconstriction of the coronary arteries and to a resulting ischemia of the hearth muscles. Peptic ulcer, another common affliction of modern man, is related to an over-secretion of hydrochloric acid and abnormal gastric activity.

Up to now, the functional state of the autonomic nervous system could be estimated only roughly through a qualitative evaluation of some existing dysfunction caused by an imbalance between the two divisions of the system:

An increased parasympathetic functioning can be noticed by a pupillary constriction, and accommodation of optic muscles; by increased secretion of the submaxillary, sublingual, and lacrimal glands; by inhibition of cardiac functions and coronary vasoconstriction; by constriction of bronchial musculature; by increased peristalsis of the digestive tract and increased secretion of hydrochloric acid in the stomach; by inhibition of anal and vesical (urinary) sphincter muscles; by vasodilatation of cutaneous vessels.

Respectively, an excitation of sympathetic functions results in dilatation of the pupils, increase in salivary and lacrimal gland secretions, an acceleration of cardiac activity and coronary vasodilatation, dilatation of the bronchi, inhibition of peristalsis and vasoconstriction of intestinal blood vessels, contraction of anal and internal (renal) sphincters, vasoconstriction, excitation of pilomotor muscles, and secretion of sweet glands.

Consequently, there is neither an objective method for the quantitative measurement of the balance between the two divisions of the autonomic nervous system, nor one that assesses quantitatively the functional state of the system, including the level on which this balance appears.

OBJECTS AND ADVANTAGES

The object of my invention is a method for the objective quantitative measurement of the functional state of the autonomic nervous system, including the balance between its two divisions.

Accordingly, the advantages of my method are:

A. A quantitative method for a minute-long objective measurement of the functional state of the autonomic nervous system, including of the balance between its two divisions.

B. The harmless nature of this non-invasive method and the lack of side effects during or after its application render it appropriate for:

diagnosing illnesses and disorders, testing the effects of new medical drugs on human subjects, assessing the alterations in the control exerted by the autonomic nervous system caused by drug, alcohol, and nicotine abuse, assessing the alterations in the control exerted by the autonomic nervous system caused by physiological and mental stress, assessing applicant's ability to cope with severely stressful work conditions such as in occupations like astronauts, pilots, and sportsmen.

C. Since the effect of the application of the method wears out in a matter of minutes, the measurement can be repeated undetermined times, thereby allowing a follow up on the alterations in the control exerted by the autonomic nervous system caused by:

a progressing illness or disorder, the improvement of physical condition as a result of a medication or treatment, physical training.

DRAWING REFERENCE NUMERALS WORKSHEET

FIG. 1. A device showing the main embodiment of the method for measuring the functional state of man's autonomic nervous system and the balance between its two divisions, in accordance with claims 1 and 4.

11—Housing box
12—DC electric source
13—On-off switch
14—Voltage divider
15—Micro-ammeter
16—Fastening belt with VELCRO fastener
17—Set of electrodes
18—Reference electrode
19—2-conductor cable connecting box with fastening belt

SUMMARY

Using the control that the autonomic nervous system exerts on the peripheral vasomotor system, the method makes it possible to measure quantitatively the functional state of the autonomic nervous system, including the balance between its two divisions. In essence, the method is an iontophoretic application of different concentrations of the two natural mediators produced by the two divisions of the autonomic nervous system—the sympathetic and the parasympathetic—on man's skin in order to assess the concentration on which a vasoconstriction, and respectively a vasodilatation, of the cutaneous vessels appears. The result is an objective quantitative information for the state of the autonomic nervous system, where the difference between the concentrations of the two mediators which cause the mentioned reaction is a measure for the imbalance between the two divisions of the autonomic nervous system.

DESCRIPTION OF THE INVENTION—STRUCTURE AND OPERATION OF THE EMBODIMENT ON FIG. 1

FIG. 1 shows a device as the main embodiment of the method for objectively measuring the functional state of man's autonomic nervous system and the balance between its two divisions in accordance with claims 1 and 4.

Structure: The device includes two sub-units:
- a. a housing box 11, comprising: a DC electric source 12, an on-off electric switch 13, a voltage divider 14 (as an example of electric current controlling devices), and a micro-ammeter 15 (as an example of electric current measuring devices),
- b. a fastening belt with VELCRO fastener 16, comprising: a set of a predetermined number of stainless-steel electrodes with a diameter of about 8 mm 17, each of them covered by a circle of filter-paper with the same diameter (not shown), a stainless-steel reference electrode 18, covered with electrically conductive matter, for instance a moistened cotton cloth (not shown), with a surface approximately the size of the area equal to the sum of the number of electrodes, and a 2-conductor cable 19, connecting box 11, with fastening belt 16.

Operation—Flowchart:
- a. Covering each electrode of set of electrodes 17 with a filter paper circle,
- b. Moistening one of the lines of the filter paper circles with diminishing by about one order concentrations of noradrenaline (for instance epinephrine supplied by ESI Pharmaceuticals), and the other line—with corresponding concentrations of acetylcholine (for instance supplied by Johnson & Johnson's IOLAB Pharmaceuticals), both drugs being representatives of sympathomimetic and parasympathomimetic drugs;
- c. Moistening with water covered with cotton cloth reference electrode 18, thus creating electric conductive matter;
- d. Attaching fastening belt 16 to a surface of the human body;
- e. Turning the electric current on supplied by DC electric source 12, by on-off switch 13, and adjusting it to approximately 8 microampers per electrode by voltage divider 14 under the control of micro-ammeter 15, the electric current is being supplied from housing box 11 to fastening belt 16 including set of electrodes 17 and reference electrode 18 by 2-conductor cable 19;
- f. Removing fastening belt 16 together with set of electrodes 17, the attached filter paper circles, and reference electrode 18 after about 1 minute;
- g. Visually or instrumentally assessing the concentrations of noradrenaline and acetylcholine at which a vasoconstriction, and respectively, a vasodilatation appears. Interpretation: Since one line of set of electrodes 17 iontophoretically supplies diminishing by about one order concentrations of the mediator of the sympathetic nervous system, noradrenaline, and the other line supplies the same concentrations of the mediator of the parasympathetic nervous system, acetylholine, the level of concentrations which cause a vasoconstriction, respectively a vasodilatation of the cutaneous vessels determine the functional state of the autonomic nervous system. The difference between the concentrations of the two mediators causing the reaction mentioned determines the degree of imbalance between the two divisions of the autonomic nervous system.

CONCLUSION, RAMIFICATIONS AND SCOPE OF INVENTION

The method is the only one which makes it possible to measure, objectively and quantitatively, the functional state of the autonomic nervous system, including the balance between its sympathetic and parasympathetic divisions.

The concentrations of the mediators causing vasoconstriction and respectively—vasodilatation—of the cutaneous vessels can be measured not only visually, but also instrumentally through the use of conventional spectrophotometric devices such as: SM-210 hand held CCD spectrophotometer, a product of CVI Spectral Instruments, PC2000 Miniature Fiber Optic Spectrophotometer, produced by Ocean Optics, or a 32-band color-measuring device, a product of Lucite Technologies, Inc. The same effect can also be assessed trough the use of a resistance-measuring device to measure the conductivity of the skin at the sites where the mediators had been applied.

The DC electric source can be a AC to DC adapter.

The above mentioned moistened cotton cloth, used as electrically conductive matter, can be substituted with conventional electrode gel for instance Spectra 360 from Parker Laboratories, Inc.

The harmless nature of this non-invasive method and the lack of side effects during or after its application render it appropriate not only for diagnostics of illnesses and disorders, but also for testing the effects of new medical drugs on human subjects. It can also be used in cases of drug, alcohol, and nicotine abuse, physiological and mental stress, as well as for the selection of men who would be able to cope with the severely stressful work conditions of occupations such as astronauts, pilots, and sportsmen. Since the effect of the application of the method wears out in a matter of minutes, the measurement can be repeated undetermined times, thereby allowing a follow up on the development and the alterations caused by a progressing illness or disorder. In this manner it also can trace the improvement of physical condition as a result of a medical treatment or physical training.

The objective and quantitative measurement of the functional state of the autonomic nervous system, including the balance between its sympathetic and parasympathetic divisions can be complemented by an iontophoretic application of sympatholitic and parasympatholitic drugs. This offers information about the functional stability of the autonomic nervous system and its two divisions.

The scope of the invention should be determined not by the embodiment illustrated, but by the appended claims and their legal equivalent.

I claim:

1. A non-invasive method for quantitative measurement of the functional state of the autonomic nervous system, including the balance between its sympathetic and parasympathetic divisions, comprising the steps of:
- a. attaching a fastening belt to a surface of the human body, said fastening belt comprising a set of a predetermined number of electrodes with a predetermined diameter, covered with filter paper circles soaked with predetermined concentrations of substances selected from the group consisting of sympathomimetic and parasympathomimetic drugs, and a reference electrode covered with electrically conductive matter,
- b. applying iontophoretically said predetermined concentration of substances selected from the group consisting of sympathomimetic, and parasympathomimetic drugs on a surface of the human body by means of an electric current of predetermined micro-amperes supplied by a housing box comprising a DC electric source, an on-off switch, a device selected from the group consisting of electric current regulating means, a device selected from the group consisting of electric current measuring means, further a 2-conductor cable supplying said electric current to the electrodes of said fastening belt, c. assessing visually the concentration under which a change of the skin color caused by vasoconstriction and respectively vasodilatation of the cutaneous vessels appears, whereby an objective quantitative method for diagnosing illnesses and disorders, for testing the effect of new medical drugs on human subjects, for assessing the damage caused by drug, alcohol, and nicotine abuse, as well as by physiological and mental stress, and for the selection of men appropriate for severely stressful occupations such as astronauts, pilots, and sportsmen, is offered.

2. The method of claim 1, further including an instrumental assessing of said concentrations of sympathomimetic and parasympathomimetic drugs, under which vasoconstriction and respectively vasodilatation of the cutaneous vessels appears, by measuring means selected from the group consisting of spectrophotometric, color-measuring, and resistance-measuring devices.

3. The method of claim 1, wherein said quantitative measurement of the functional state of the autonomic nervous system is carried out by means of said iontophoretic applying of substances selected from the group consisting of sympatholitic and parasympatholitic drugs.

4. A device, as a measuring means for a non-invasive measurement of the functional state of the autonomic nervous system, including the balance between its sympathetic and parasympathetic divisions, based on an iontoforetic application of predetermined concentrations of substances selected from the group consisting of sympathomimetic, and parasympathomimetic drugs on a surface of the human body, comprising:

a. a fastening belt, comprising a set of a predetermined number of electrodes with a predetermined diameter, covered with filter paper circles soaked with said predetermined concentrations of substances selected from the group consisting of sympathomimetic, and parasympathomimetic drugs, and a reference electrode covered with electrically conductive matter, b. a housing box comprising a DC electric source, an on/off switch, a device selected from the group consisting of electric current regulating means, a device selected from the group consisting of electric current measuring means, a 2-conductor cable connecting said fastening belt with said housing box allowing said iontophoretic application of predetermined concentrations of substances selected from the group consisting of sympathomimetic, and parasympathomimetic drugs on said surface of the human body by means of an electric current of predetermined micro-amperes, c. a visual assessment of the concentrations under which a change of the skin color caused by vasoconstriction and respectively vasodilatation of the cutaneous vessels appears, whereby said device is appropriate for an objective and quantitative measurement of the functional state of the autonomic nervous system, for diagnosing illnesses and disorders, for testing the effect of new medical drugs on human subjects, for assessing the damage caused by drug, alcohol, and nicotine abuse, as well as by physiological and mental stress, and also for the selection of men appropriate for severely stressful occupations such as astronauts, pilots, and sportsmen.

5. The device of claim 4, further including measuring means selected from the group consisting of spectrophotometric, color-measuring, and resistance-measuring devices by means of an instrumental measurement of said concentrations, under which vasoconstriction and respectively vasodilatation of the cutaneous vessels appears.

6. The device of claim 4, wherein said means for quantitative measurement of the functional state of the autonomic nervous system, including the balance between its sympathetic and parasympathetic divisions are substances selected from the group consisting of sympatholitic and parasympatholitic drugs.

\* \* \* \* \*